(12) United States Patent
Miller

(10) Patent No.: US 9,414,902 B2
(45) Date of Patent: Aug. 16, 2016

(54) METHOD FOR TREATING PROLAPSE AND INCONTINENCE

(75) Inventor: Dennis Miller, Whitefish Bay, WI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 672 days.

(21) Appl. No.: 12/939,832

(22) Filed: Nov. 4, 2010

(65) Prior Publication Data

US 2011/0105836 A1 May 5, 2011

Related U.S. Application Data

(60) Provisional application No. 61/258,001, filed on Nov. 4, 2009.

(51) Int. Cl.
 *A61F 2/02* (2006.01)
 *A61F 2/00* (2006.01)

(52) U.S. Cl.
 CPC .................... *A61F 2/0045* (2013.01)

(58) Field of Classification Search
 CPC ........... A61F 2/00; A61F 2/02; A61F 2/0004; A61F 2/0031; A61F 2/0036; A61F 2/0045
 USPC ................................ 600/29–30, 37
 See application file for complete search history.

(56) References Cited

U.S. PATENT DOCUMENTS

| | | | |
|---|---|---|---|
| 6,575,897 B1 * | 6/2003 | Ory ....................... | A61F 2/0045 600/30 |
| 6,695,855 B1 * | 2/2004 | Gaston ............... | A61B 17/0469 600/29 |
| 7,985,173 B2 | 7/2011 | Jacquetin | |
| 7,985,174 B2 | 7/2011 | Nicita | |
| 7,998,055 B2 | 8/2011 | Siegel et al. | |
| 8,057,382 B2 * | 11/2011 | Thierfelder et al. | 600/30 |
| 8,109,867 B2 | 2/2012 | Rosenblatt | |
| 8,262,557 B2 * | 9/2012 | Chapman et al. | 600/37 |
| 2002/0095181 A1 * | 7/2002 | Beyar | 606/232 |
| 2002/0183588 A1 * | 12/2002 | Fierro | 600/30 |
| 2005/0101834 A1 * | 5/2005 | Merade | 600/37 |
| 2007/0173864 A1 | 7/2007 | Chu | |
| 2007/0270890 A1 | 11/2007 | Miller | |
| 2008/0119863 A1 * | 5/2008 | Mellier | 606/99 |
| 2008/0146886 A1 * | 6/2008 | Lucas | 600/220 |
| 2009/0171143 A1 * | 7/2009 | Chu et al. | 600/37 |
| 2009/0216075 A1 * | 8/2009 | Bell et al. | 600/37 |
| 2009/0326573 A1 * | 12/2009 | Miller | 606/193 |
| 2012/0083807 A1 | 4/2012 | Mathisen et al. | |
| 2012/0108894 A1 | 5/2012 | Young et al. | |
| 2013/0006050 A1 | 1/2013 | Rane et al. | |

FOREIGN PATENT DOCUMENTS

WO 2007106897 A2 9/2007

* cited by examiner

*Primary Examiner* — Charles A Marmor, II
*Assistant Examiner* — Thaddeus Cox

(57) ABSTRACT

A system and method of treating vaginal prolapse and incontinence comprises a kit. The kit includes a mesh graft configured for attachment to the anterior and posterior vaginal walls to thereby treat the vaginal prolapse. A graft delivery device is also provided for introducing and placing the mesh graft to a location deep within the peritoneal cavity and for attaching the graft thereto. A leg assembly is provided and coupled to an end of the mesh graft and cooperates with the graft delivery device to anchor and affix the mesh graft to the desired anatomical structures. The method according to the present invention contemplates a laparoscopic graft placement utilizing the components of the kit.

17 Claims, 17 Drawing Sheets

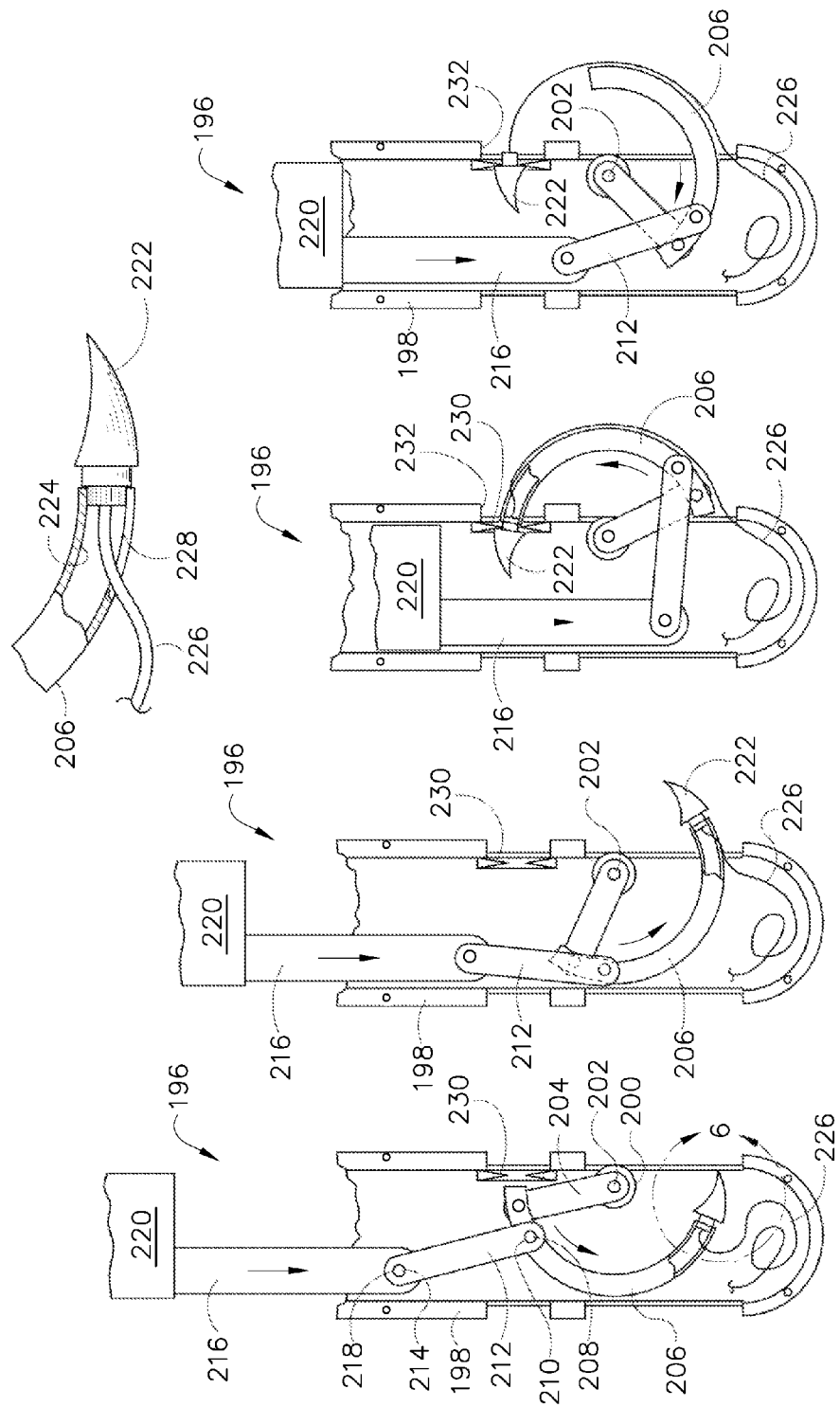

```
┌─────────────────────────────────────────┐
│   Forming an abdominal access to the vagina   │
└─────────────────────────────────────────┘
                    ↓
┌─────────────────────────────────────────┐
│   Denuding a peritoneum over an anterior and  │
│        posterior vaginal wall fascia          │
└─────────────────────────────────────────┘
                    ↓
┌─────────────────────────────────────────┐
│ Inserting at least one mesh graft and leg assembly │
│    through the abdominal access to the vagina      │
└─────────────────────────────────────────┘
                    ↓
┌─────────────────────────────────────────┐
│  Attaching at least one panel of the mesh graft to │
│         the anterior vaginal wall fascia           │
└─────────────────────────────────────────┘
                    ↓
┌─────────────────────────────────────────┐
│  Attaching at least one panel of the mesh graft to │
│        the posterior vaginal wall fascia           │
└─────────────────────────────────────────┘
                    ↓
┌─────────────────────────────────────────┐
│   Creating a tunnel in the peritoneum between a    │
│         first incision and a second incision       │
└─────────────────────────────────────────┘
                    ↓
┌─────────────────────────────────────────┐
│     Passing the leg assembly through the tunnel    │
└─────────────────────────────────────────┘
                    ↓
┌─────────────────────────────────────────┐
│  Anchoring a mesh extension of the mesh graft to a │
│          soft tissue near a sacral promontory      │
└─────────────────────────────────────────┘
                    ↓
┌─────────────────────────────────────────┐
│     Passing the leg assembly through the tunnel    │
└─────────────────────────────────────────┘
                    ↓
┌─────────────────────────────────────────┐
│         Adjusting a tension of the mesh graft      │
└─────────────────────────────────────────┘
```

FIG. 25

METHOD FOR TREATING PROLAPSE AND INCONTINENCE

CROSS-REFERENCE TO RELATED APPLICATIONS

This application claims priority from U.S. Provisional Patent Application Ser. No. 61/258,001, filed on Nov. 4, 2009, the entirety of which is expressly incorporated by reference herein.

BACKGROUND OF THE INVENTION

The present invention relates in general to a system and method in the field of prolapse treatment. More particularly, the present invention relates to a system with multiple components, and a method for surgically correcting tissue wall prolapse using the same. Specifically, a preferred embodiment of the present invention is a kit that has the following components: a pre-cut shaped mesh graft and a graft delivery device.

As is known to those skilled in the art, the treatment of vaginal wall prolapse has been hampered by high failure rates. The main reasons for failure have been the inherent weakness of the tissue being re-approximated and the inability of the repaired tissue to withstand the forces applied by the abdominal cavity bearing down from above. In the last decade, one major advance has been the addition of grafts to reinforce those repairs. While this phenomenon has been gaining widespread acceptance, there lacks a consensus regarding how to affix the graft under the vaginal wall to best maintain durability and vaginal caliber.

A number of prior art patents and publications are directed to various methods of treating and preventing recurring vaginal wall prolapse. For instance, U.S. Pat. No. 6,102,921 (the "'921 patent"), incorporated herein by reference, discloses a mesh graft material for treating vaginal prolapse. Further, U.S. Pat. No. 6,638,284 discloses an apparatus configured for delivering a mesh graft like that of the '921 patent for treating vaginal wall prolapse.

The most commonly accepted procedure for surgical treatment of pelvic organ prolapse is an abdominal sacrocolopopexy (ASC). The procedure was originally described as being performed through an open incision, i.e., laparotomy, wherein one end of a wide graft was attached to the vagina with multiple sutures and the other end attached to the sacral promontory after opening the enclosing tissue layer known as the peritoneum. The procedure has been refined over the years and has multiple subtle variations. It is acknowledged that the procedure, as described, has several limitations and, as such, the procedure is not utilized by all surgeons despite its overall level of success as compared to other treatments. For example, opening the peritoneum and sewing within the retroperitoneal space requires special skill and there is significant risk of bleeding. In addition, it is particularly challenging to apply the correct amount of tension to the graft needed to elevate the vagina and then fixate the graft at that tension.

Further, this approach has been associated with an increased risk of serious bowel complications, including potentially life threatening bowel obstruction. To avoid these complications, some surgeons have begun to attempt this procedure laparoscopically, at times employing known robotic techniques. However, this also creates a number of technical challenges as laparoscopic knot tying is a skill possessed by only a limited number of surgeons.

One alternative treatment approach for prolapse has been to introduce the mesh transvaginally. The evolution of transvaginal mesh procedures has produced several deployment devices to increase safety and make the procedures accessible to more surgeons. One procedure includes the use of a Pinnacle® device, made by Boston Scientific Corporation, having a dilator for bringing the mesh into place along with a limited access suture capture device (known commercially as a Capio®, made by Boston Scientific Corporation). However, some surgeons prefer to not introduce the mesh directly through the vagina due to potential inherent infectious and sexual complications associated with transvaginal introduction. PCT publication WO/2007/109508 discloses a method and system for treating vaginal wall prolapse by transvaginal insertion of a mesh graft, and is herein incorporated by reference.

Accordingly, it has been desired to provide a device and method of treating vaginal prolapse that combines the ease of use of the transvaginal meshes, and in particular, leveraging a suture capture device and Pinnacle®-like dilators to employ the mesh laparoscopically, with the known advantages of the ASC procedure, i.e., ease of reaching internal structures necessary for implementing the mesh. Enhancements to the shape of the graft and the method of attachment to both the vagina and the sacrum provide increased safety and ease of use. The present invention eliminates the need to suture the graft to the sacrum. These enhancements thereby allow a greater number of patients to be treated using a minimally invasive prolapse treatment.

SUMMARY AND OBJECTS OF THE INVENTION

The present invention is directed to a system and method for preventing recurring prolapse. The system preferably includes a multiple component kit comprising a graft delivery device that is modified for use with the method of the present invention. For example, a Capio® device, or similar such device, may be utilized in practicing the method of the present invention. The kit further includes a mesh graft having a narrow extension and a body configured to cover both the anterior and posterior wall of the vagina. The precut mesh may be a single joined piece composed of an anterior body and a posterior body connected in the extension or may be two separate meshes, both with narrow extensions. The novel advantage of the two separate meshes is to provide independent adjustment of the anterior and posterior walls. With a wide body mesh, it would be impractical to have two separate pieces lying over each other and having increased mesh load. The narrow extensions make it possible to have two independent pieces and still have low mesh load and avoid overlap. One configuration of the mesh pieces is to have a slightly wider top of the extension for suturing to the sacrum if the self-affixing dilator is not included. The body of the mesh may include fixation tips configured for attachment to the vagina. The narrow extension portion of the mesh graft includes a dilator configured to adjustably couple the mesh graft to the sacrum without requiring the surgeon to tie down the sutures. The dilator preferably has a suture leader at one end thereof. One object of the invention is to provide a method for treating recurring prolapse that is predictable and reproducible, thereby increasing success rates and decreasing pain, variance, recovery time, and costs. Another object of the invention is to provide a method that has one or more of the characteristics discussed above but which is relatively simple to set up and perform.

The method of the present invention is preferably directed to a laparoscopic method of employing a mesh graft for treating and preventing recurring vaginal prolapse. Alternatively, the method of employing the mesh graft according to the present invention could be done through an incision.

These and other aspects and objects of the present invention will be better appreciated and understood when considered in conjunction with the following description and the accompanying drawings. It should be understood, however, that the following description, while indicating preferred embodiments of the present invention, is given by way of illustration and not of limitation. Many changes and modifications may be made within the scope of the present invention without departing from the spirit thereof, and the invention includes all such modifications.

BRIEF DESCRIPTION OF THE DRAWINGS

A clear conception of the advantages and features constituting the present invention, and of the construction and operation of typical mechanisms provided with the present invention, will become more readily apparent by referring to the exemplary, and therefore non-limiting, embodiments illustrated in the drawings accompanying and forming a part of this specification, wherein like reference numerals designate the same elements in the several views, and in which:

FIGS. 8-11 are partial side elevation cross-sections illustrating the operation of the graft placement component having a bullet needle and thread attached thereto;

FIG. 12 is a partial top elevation view of the graft placement component of the present invention and the bullet needle thereof;

FIG. 25 is a flow chart illustrating the method of treating vaginal prolapse according to the present invention.

Figure 1:
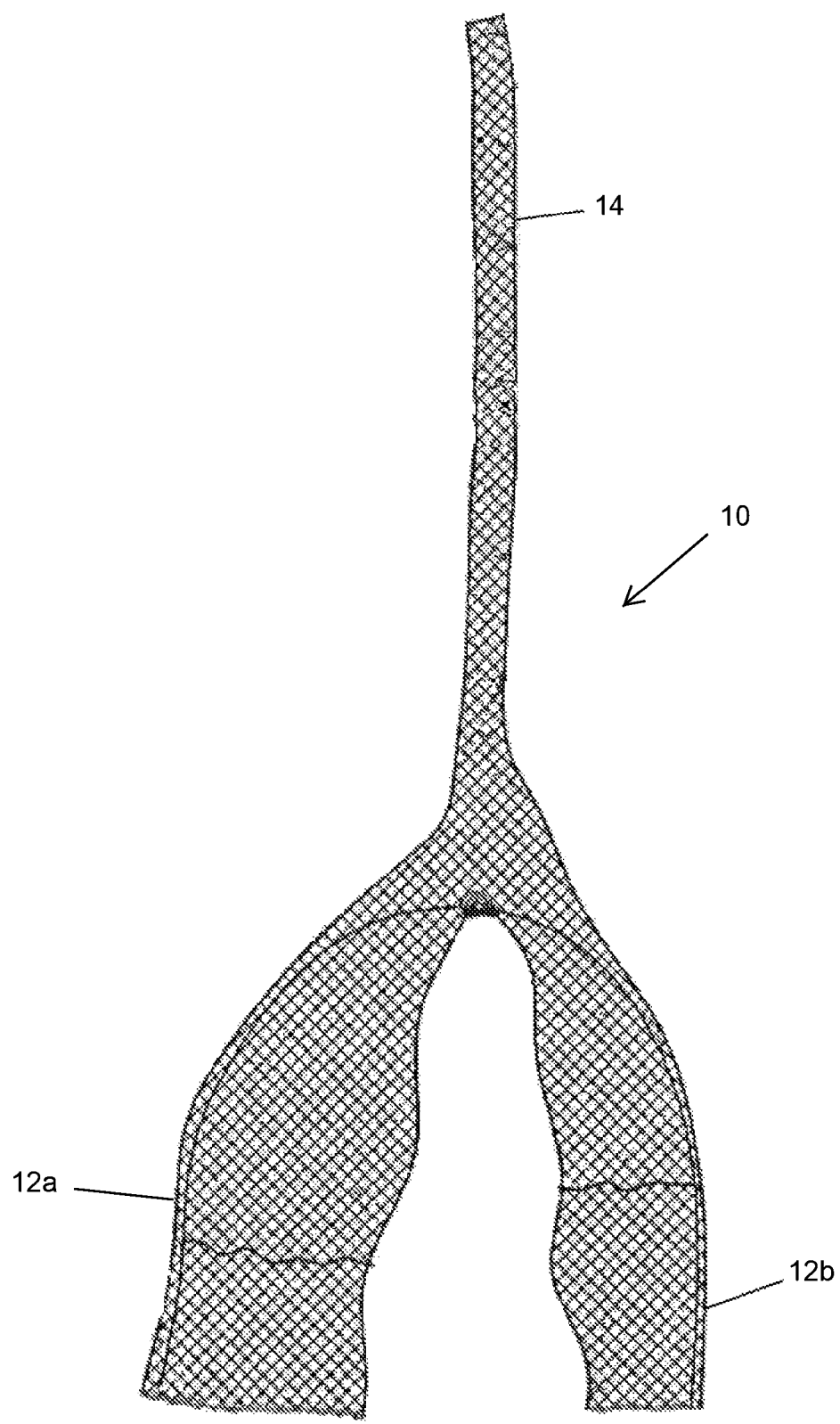
FIG. 1 is a top plan view of a mesh graft for treating vaginal prolapse according to the present invention.

In describing the preferred embodiment of the invention that is illustrated in the drawings, specific terminology will be resorted to for the sake of clarity. However, it is not intended that the invention be limited to the specific terms so selected and it is to be understood that each specific term includes all technical equivalents that operate in a similar manner to accomplish a similar purpose. For example, the word "connected" or terms similar thereto are often used. They are not limited to direct connection but include connection through other elements where such connection is recognized as being equivalent by those skilled in the art.

DESCRIPTION OF EMBODIMENTS

1. System Overview

The present invention is directed to a novel system and method for treating vaginal wall prolapse. The system, according to the present invention, preferably includes a kit comprising a graft, a graft placement/delivery device, and a leg assembly including a dilator and sheath. The graft, according to the present invention, can have several different configurations, i.e., shapes and structure, and may be made from a variety of materials including a pre-cut mesh and a dermis, as is generally understood in the art.

The mesh graft of the present invention preferably includes attached bullet needles for attaching the mesh graft to accepted anatomic structures without having to travel through unfamiliar pathways such as, the ischiorectal fossa and obturator membrane. Instead, the surgeon is able to couple the mesh graft to a desired location directly through a laparoscopic incision made in the abdominal wall of the patient. The mesh graft, according to the present invention, is preferably configured to reach the sacral promontory or any chosen site on the sacrum. The body of the mesh graft preferably includes narrow mesh extension for attachment thereto. The mesh shape, according to the present invention, decreases mesh load without sacrificing strength. Further, a narrow mesh extension is easier to insert than a uniformly wide mesh.

The second component of the kit, according to the present invention, is preferably the graft placement component or delivery device. The inventive delivery device is preferably a blade trocar of the kind generally known in the art. For instance, devices sold under the names "Laurus®" or "Capio®" may be modified for use with the kit of the present invention. The graft delivery device preferably acts as a suture-capturing device, wherein the suture is preferably a wing of a mesh graft according to the present invention. Preferably, the graft placement device is configured such that a shaft thereof is capable of reaching a desired location at the sacral promontory.

Using the components described above, the inventive method includes the following steps. Preferably, the procedure, according to the present invention, is done laparoscopically; however, it may also be performed via a traditional incision. Regardless of the approach, the abdomen is entered and the vagina is pushed inward with the use of an instrument adapted to stretch and increase access to the overlying vaginal peritoneum. For instance, a vaginal-shaped paddle adapted for insertion into the vagina may be used. The paddle may include a flat end opposite a handle. The flat end is preferably sized and shaped to cooperate with the vagina, as is generally understood. The handle is preferably constructed from a metal or plastic rod and is relatively thin for allowing relatively easy manipulation thereof. One configuration of the rod would have a 30 degree angulation to facilitate introduction into the vaginal canal.

The peritoneum is peeled back exposing the vaginal fascia to be used for anchoring. The graft or mesh body assembly is introduced into the abdomen and positioned proximate both of the vaginal surfaces, i.e., the anterior and posterior vaginal walls. The mesh is attached to the fascia either by way of a suture or by utilizing any known fixation method generally known in the art, such as those seen in "Quill" sutures. Preferably, the suture is directly attached to the mesh body utilizing a knot-free bidirectional fixation. That is, the suture is preferably directly preattached to the mesh body. A vaginal apex suture is affixed to the area where both meshes meet. The area of the sacrum is then exposed and a pair of small incisions is made in the peritoneum. The first incision is preferably made over the promontory, though the first incision may also be made slightly lower such as over the S1 or S2 vertebrae. The second incision is made just above the posterior cul-de-sac and a narrow channel (tunnel) is created therebetween. Alternatively, the channel can be created through the vaginal incision and guided by laparoscopic view up to the upper pole of the channel (tunnel). The graft delivery device is introduced through the peritoneal channel and then withdrawn, thereby bringing the narrow mesh extension over the desired point of fixation. Next, the mesh wings are attached to a suture-capturing device via the bullet needle and suture leader thereof. The wing of the mesh is inserted and the needle and suture device are inserted through an opening over the sacrum. The wing and bullet needle is then inserted through the connective tissue and, in some cases, the longitudinal ligament. The wing is then pulled back through the laparoscopic trocar. The bullet needle is then released from the suture device. Next, the suture, the dilator, and the sheath are pulled through the fixation point until the mesh is wedged into the fixation point. The mesh may then be adjusted for a precise tension. By allowing for a tension-free attachment, the mesh may be adjusted for each individual patient that would not be possible with suture fixation. The excess wing material may then be trimmed away and simply discarded. Because the peritoneal openings are relatively small, they do not require closure thereof.

2. Detailed Description of the Preferred Embodiments

Figures 2, 3:
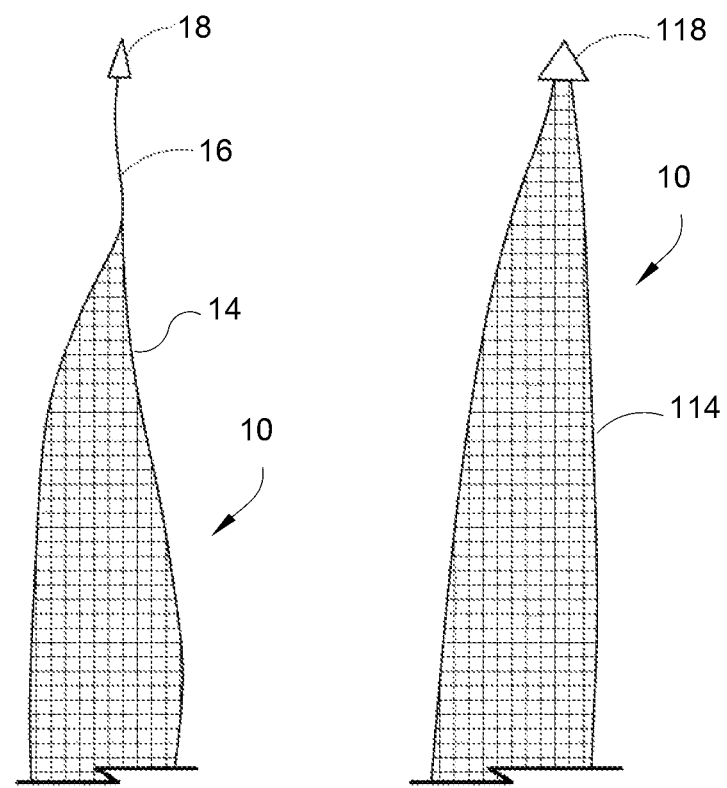
FIG. 2 is a partial top plan view of another embodiment of the mesh graft of the present invention including an attachment means for coupling the mesh graft to a vaginal wall.
FIG. 3 is a partial top plan view of an alternative embodiment of the mesh graft of the present invention illustrated in FIG. 2.
Figure 4:
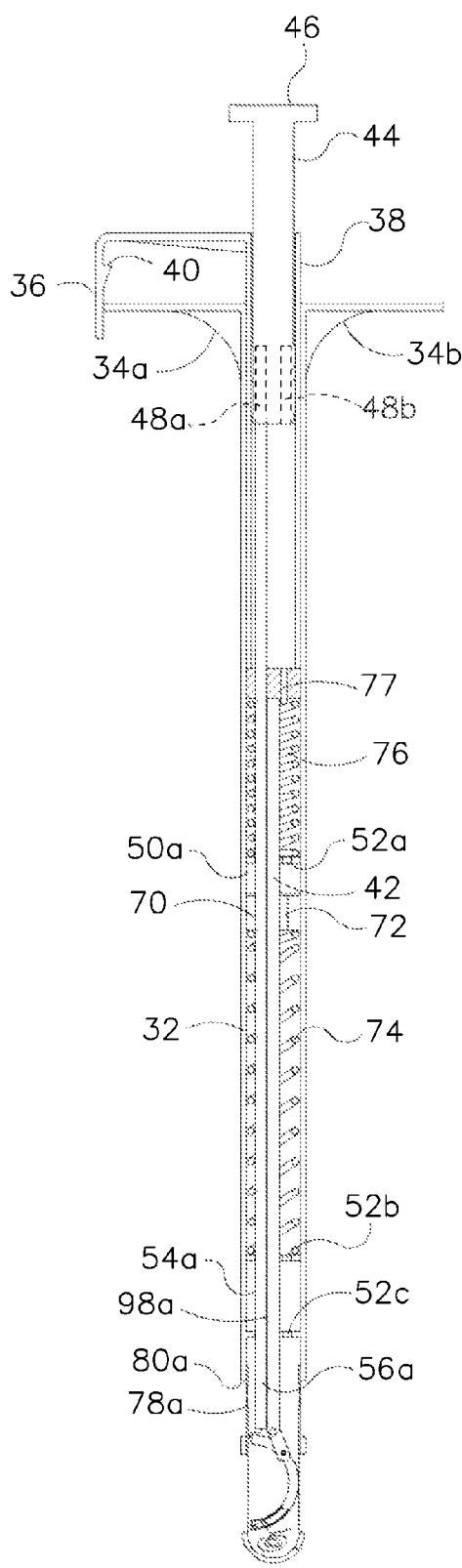
FIG. 4 is a side elevation cross-section of a preferred embodiment of a mesh placement component according to the present invention.
Figure 14:
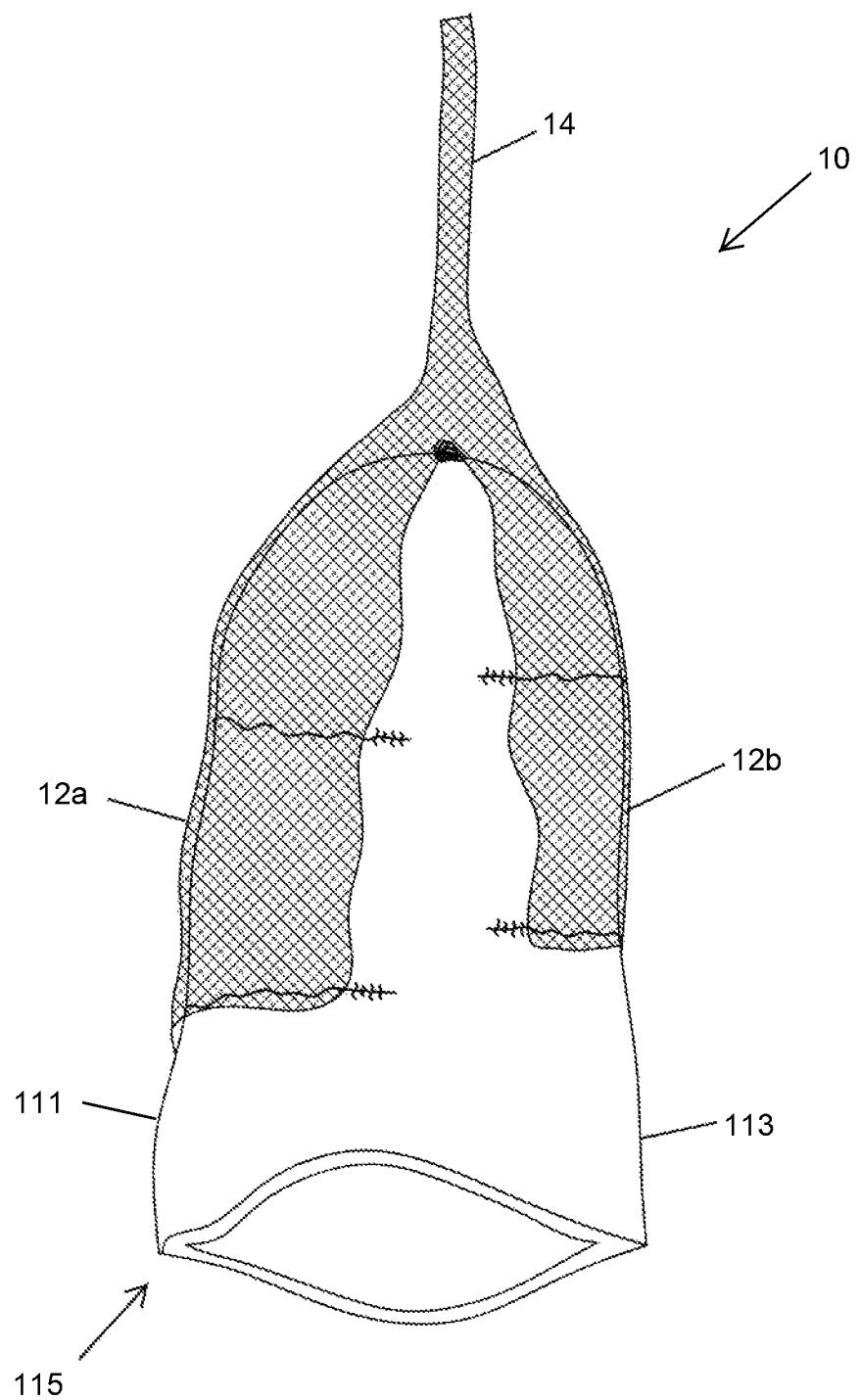
FIG. 14 is a perspective view of the mesh graft of the present invention applied to a posterior wall of a vagina.

Referring now to the drawings, and initially to FIGS. 1-3, a graft mesh 10 (mesh) according to the present invention is illustrated. The mesh 10 is configured for providing support to the vaginal walls, as will be discussed herein in detail. The mesh 10 has a pair of panels, legs or wings 12a, 12b, and a mesh extension 14 that extends from a central portion of the mesh 10. The mesh 10, according to the present invention, is preferably sized and shaped to conform to the vaginal wall shape. As illustrated in FIGS. 1 and 14, wing 12a, when configured to conform to the anatomical contours of the anterior vaginal wall, may be larger than wing 12b, which is configured to conform to the anatomical contours of the posterior vaginal wall. The legs or wings of mesh 10 may be affixed directly to the vaginal wall. In one embodiment, wings 12a, 12b are sutured directly to the vaginal wall by means of knot-free bidirectional fixation sutures, or any similar fixation means known in the art. Multiple sutures or alternative fixation means may be employed on each leg or wing to ensure a secure fixation between the mesh and the vaginal wall.

The mesh extension 14 preferably includes means for drawing the mesh 10 through the ligaments and other tissue and for attaching the mesh 10 thereto. In particular, the mesh extension 14 preferably includes a suture portion 16 extending longitudinally away from the mesh extension 14. The suture portion 16 terminates in a bullet needle 18 of the kind generally known in the art. The mesh extension 14 is intended to be used for attachment to anatomical structures located deep within the pelvis making them excellent for support but otherwise difficult to access without a special graft delivery device, as will be described more fully below. However, once such a device reaches the preferred location, the device helps the surgeon to wedge the graft mesh into place.

Turning now to FIGS. 2-3, various preferred configurations of the mesh 10 according to the present invention are illustrated. In FIG. 2, the bullet needle 18 is relatively small and generally round and is connected to the mesh extension 14 via suture portion 16 which comprises a thread or very thin segment of mesh. In FIG. 3, e.g., the bullet needle 118 is bigger, as compared to the bullet needle 18 of FIG. 2. The bullet needle 118 is generally round and is connected to the mesh extension 114 via a segment of mesh 10. While the mesh 10 is preferably shaped, as shown in FIGS. 1-3, the mesh may be of any suitable shape and generally will incorporate a central body portion and at least two panels 12a, 12b for attaching to the vaginal walls. The mesh of the present invention may be produced in a substantially oval shape or trapezium shape with extension arms and legs extending away from the central body portion of the mesh. The mesh is configured in this way so that it can be easily positioned over the pubocervical fascia and secured via the surrounding ligaments. Alternatively, the bullet needle 18, 118 may be more densely-formed mesh material. In such an embodiment, the small stainless steel needles may be replaced altogether. See, e.g., U.S. App. Pub. No. 2006/0052801.

Figure 19:
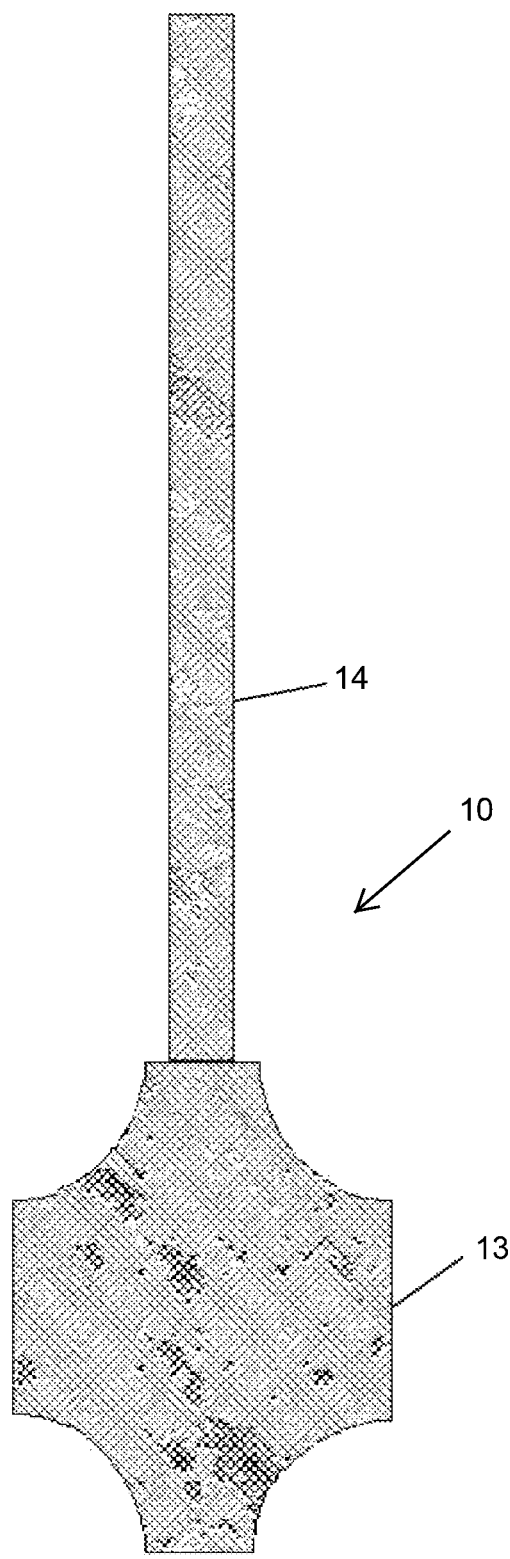
FIG. 19 is a top plan view of an illustrative embodiment of an anterior mesh graft for treating vaginal prolapse according to the present invention wherein the anterior mesh graft is configured to be applied to the anterior wall of a vagina.
Figure 20:
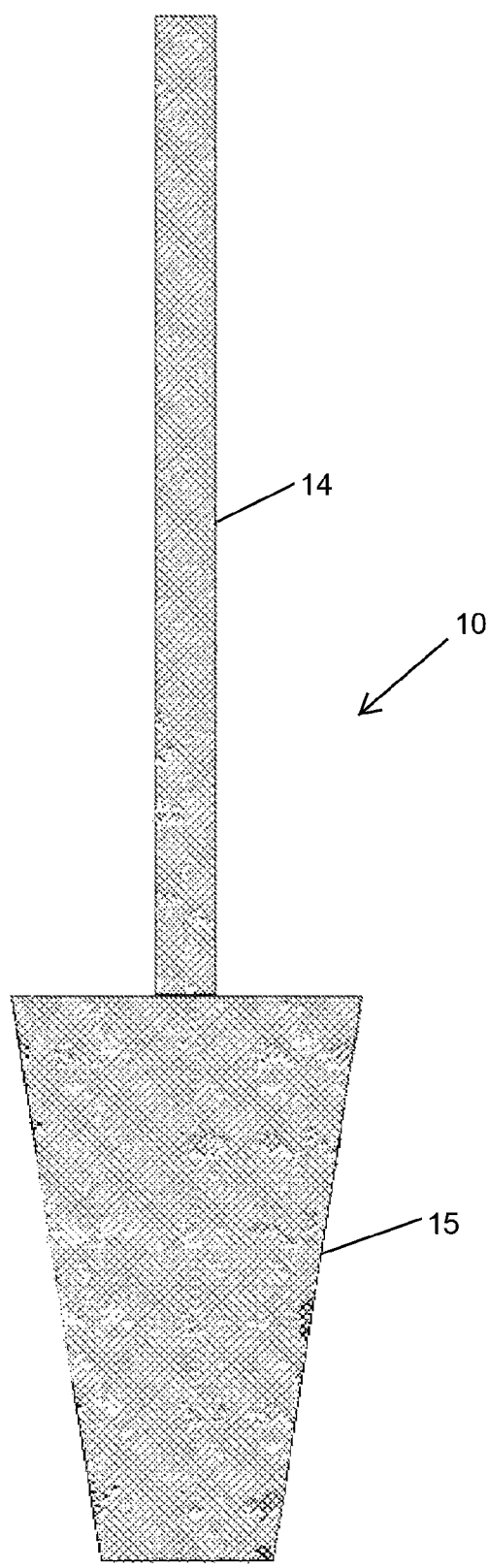
FIG. 20 is a top plan view of an illustrative embodiment of a posterior mesh graft for treating vaginal prolapse according to the present invention wherein the posterior mesh graft is configured to be applied to the posterior wall of a vagina.

In an alternative embodiment, two distinct grafts may be used for providing support to the vaginal walls, as described herein. As illustrated in FIG. 19, a mesh 10 may be configured to exclusively affix to the anterior vaginal wall. The mesh 10 of FIG. 19 includes a panel 13 configured to be secured to an anterior wall of a vagina. The panel may have a roughly rectangular configuration with reduced corners, as to ensure increased surface area contact between the panel 13 and the anterior vaginal wall. The mesh extension 14 of FIG. 19 is intended to be used for attachment to anatomical structures located deep within the pelvis, as discussed herein. Additionally, as illustrated in FIG. 19, a mesh 10 may be configured to exclusively affix to the posterior vaginal wall. The mesh 10 of FIG. 20 includes a panel 15 configured to be secured to a posterior wall of a vagina. The panel 15 may have a roughly trapezoidal configuration, with a mesh extension 14 affixed to the long base of the panel 15. The panel 15 tapers away from the mesh extension 14 as to accommodate the tapering of the posterior vaginal wall and ensure increased surface area contact between the panel 15 of the posterior vaginal wall. The mesh extension 14 of FIG. 20 is intended to be used for attachment to anatomical structures located deep within the pelvis, as discussed herein. The anterior and posterior grafts of FIGS. 19-20 may be either used individually or simultaneously for providing support to the vaginal walls. In an alternative embodiment, anterior and posterior grafts of FIGS. 19-20 may be sutured or otherwise affixed to one another at or near the vaginal apex. In such an embodiment, a single mesh extension 14 may provide a sufficient anchor to anatomical structures located deep within the pelvis as to adequately support the vaginal walls. Alternatively, multiple mesh extensions may be employed to anchor the anterior and posterior grafts of FIGS. 19-20.

The mesh material itself is preferably similar to the mesh material made by Boston Scientific Corporation called "Polyform®". Such a mesh is described in U.S. Patent Application Pub. No. 2005/0261545, incorporated herein by reference. There are many types of available mesh grafts such as the mesh described in PCT/US02/31681 to Ethicon, also incorporated herein by reference. Any known mesh can be used for this procedure. A biomaterial graft may also be substituted.

The mesh preferably includes a plurality of open pores bounded by strands made of nonwoven polymeric material, for example, a polypropylene having monofilament fibers, wherein the junctions between the strands are without open interstices and the majority of open pores in the mesh have an area of less than 15 mm². Preferably, the pore size has an area of less than 10 mm². In the most preferred embodiments, the pore size of the central body portion of the mesh is greater than the pore size of the longitudinal side portions. The pore size range in these longitudinal side portions is preferably between 3 mm and 8 mm wide. The preferred mesh is also light and very flexible having a weight of less than 0.0080 g/cm2. The materials and mesh arrangement are such so as to minimize the chance of infection after implant.

While any conventional prosthetic material currently used for the treatment of pelvic organ prolapse can be employed when performing the inventive method, there are many so-called biografts that can be used as well such as animal or human donor tissue or any other xenograft material such as pig dermis, allograft, or homograft of skin. However, while any of these materials are suitable for reinforcing the vaginal wall, a synthetic polypropylene mesh is preferred. While the mesh extension 14 is preferably affixed to a relatively small rounded bullet needle, it is also preferably tapered to allow atraumatic passage of it through the tissue and promote gripping of the wider portion of the mesh extension 14 to the surrounding tissue. Further, instead of using the needle method for attaching the graft mesh, it is also possible for the mesh to be attached by other fastening means. Such a fastening means including a medical adhesive or glue, microwave or radio frequency welding, staples, tacks, and a hook and loop-type fastener.

The second component is the graft delivery device or placement component as shown in FIGS. 4-12. One of the novel concepts in this invention is the adaptation of a previously patented suture-passing device for the graft delivery device, e.g., U.S. Pat. Nos. 5,364,408; 5,540,704; 5,458,609; 5,575,800, and 5,662,664. The modification of such a device allows the surgeon to use this device to pass the graft mesh's wings, e.g., the arms and legs, directly through the desired anchoring structures without having to traverse these pathways. Further, the inventive device itself is easier to use than the graft delivery devices currently in use in prolapse surgery. Therefore, the inventive device requires less skill to deliver the graft wings to their target location. As mentioned, the inventive delivery device is preferably based, in part, on the "Capio®" device (see e.g., patent numbers above) which is sold by Boston Scientific. See also, e.g., U.S. Pat. Application Pub. No. 2006/0052801. The Capio® device was originally patented as the Laurus device and is generally used elsewhere for suture passage and placement in limited access cavities. The suture capture device is preferably a trocar capped by a curvilinear needle guide and a deployable bullet needle that passes to a catch mechanism. A plunger at the other end of the device deploys it.

Alternative delivery devices may be used for securing the mesh. For instance, a delivery device like that disclosed in U.S. Pat. Nos. 6,273,852 and 6,981,983 may also be used in practicing the present invention. Another such delivery device capable of use with the present invention is the Endostitch™ sold by Tyco Healthcare. Finally, surgical staples or similar such known fasteners may be used in securing the mesh and applied with delivery devices known in the art.

Detailed drawings of an illustrative embodiment of the invention are shown in FIGS. 4-12 wherein the graft delivery device 30 includes an outer housing 32, with finger grips 34a and 34b, and a deployment catch 36. The outer housing 32 is preferably made of injection molded plastic such as polycarbonate, as are many other of the components described herein. A deployment sleeve 38, slidably disposed within the outer housing 32, has a retention catch 40 and is attached to a pushrod 42, constructed, for example, of stainless steel. A driver shaft 44 includes a button 46 and has a hole 48a, into which is bonded an elongate rigid shaft 50a, and an elongate shaft 50a is secured within the hole 48a. The rigid shaft 50a, which may be made of music wire, passes through outer housing ribs 52a, 52b, and 52c, terminates slidably disposed within a hollow cylinder 54a. The hollow cylinders 54a and 54b, preferably made from stainless steel hypodermic tubing, are held in recesses in the outer housing ribs 52b and 52c. An elongate flexible tubular member 56a, that may be made of polypropylene or other suitable material, is also slidably disposed within the hollow cylinder 54a. As shown in FIG. 5b, needle guide 58a may also be constructed from stainless steel hypodermic tubing, and has pivot pins 60a and 60b pivotally disposed within outer housing bosses 62a and 62b. A driving link 64a is attached by a link pin 66 to the pushrod 42 and to the needle guide 58a by a pivot pin 68a, with the entire mechanism preferably made of stainless steel so as to maximize the biocompatibility as well as the strength of the actuating members.

Referring again to FIGS. 4 and 5, the device 30 has a driver retainer 70 that is slidably disposed within the outer housing 32, and is fixedly attached to rigid shafts 50a and 50b, with a hole 72 to allow the pushrod 42 to pass slidably therethrough. A driver spring 74, preferably wound from stainless steel wire, is compressed between the driver retainer 70 and the outer housing rib 52b. A deployment spring 76, also made of stainless steel wire, is compressed between an end 77 of the deployment sleeve 38 and outer housing rib 52a. A needle catch 78a is housed within a recess 80a in the outer housing 32.

Figure 7:
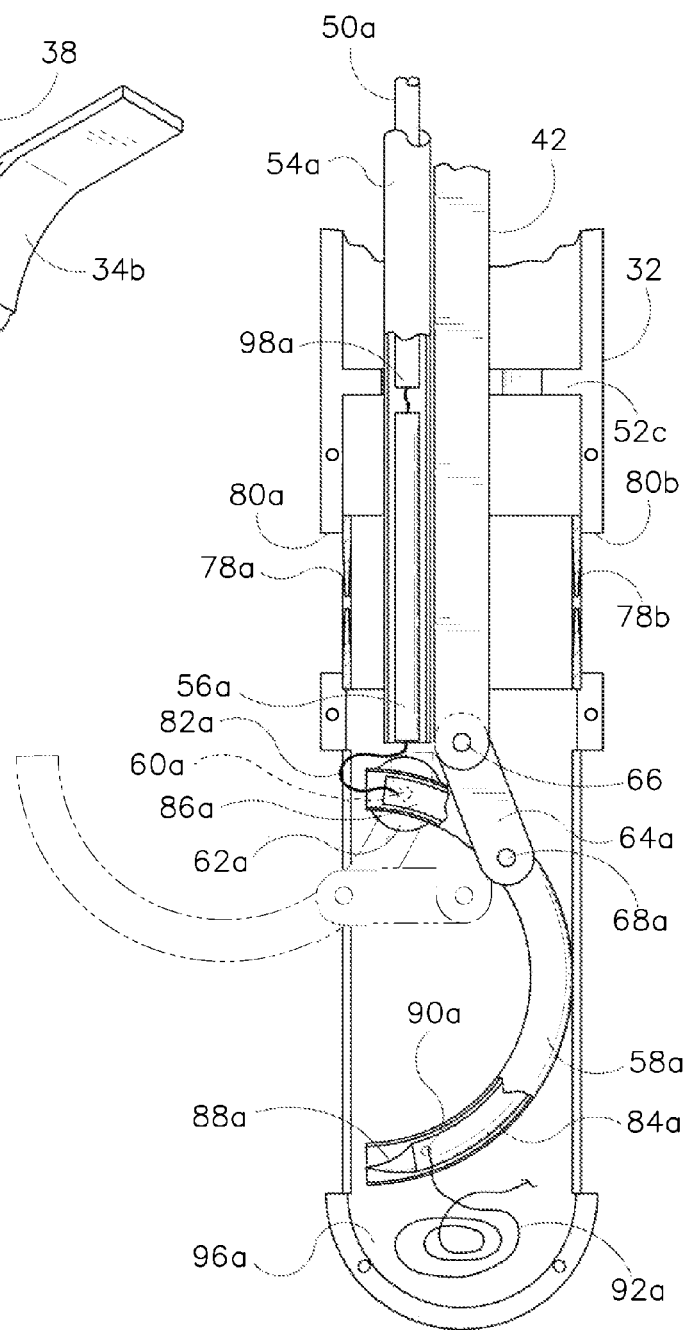
FIG. 7 is a partial perspective view of the opposite end of the mesh placement component illustrated in FIG. 6.

Referring now to FIG. 7, a retraction line 82a that is preferably made of Kevlar is slidably threaded through the flexible tubular member 56a and is attached to a needle carrier 84a by means of a crimp 86a or other means that would bind the retraction line 82a to the needle carrier 84a. The distal end of the retraction line 82a is attached to the rigid shaft 50a by means of another crimp 98a or other means. The needle carrier 84a is slidably disposed within the needle guide 58a, and holds a needle 88a (or, e.g., bullet needle 18), preferably constructed of surgical grade stainless steel in a recess 90a, such needle having a suture 92a attached thereto. The suture material is preferably polyglycolic acid, but may be made of polypropylene, nylon, silk, catgut, or any other materials known in the art selected for their biocompatibility and tensile strength to be used in the body for the approximation of tissue. The suture 92a exits the needle guide 58a by means of a groove (not shown) and is stored in a recess 96 in outer housing 32. In one preferred embodiment, suture 92a would be, e.g., suture 16 which is connected to mesh extension 14 as shown in FIGS. 1-3.

Figure 5:
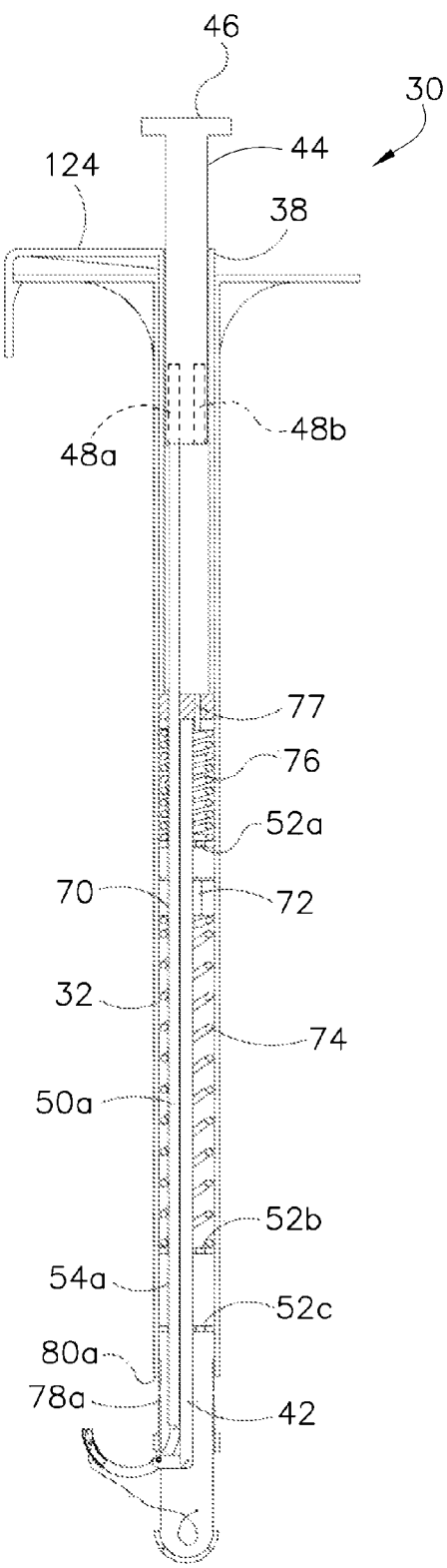
FIG. 5 is a side elevation cross-section of a preferred embodiment of the mesh placement component of FIG. 4 showing an attachment hook portion in an actuated position.
Figure 6:
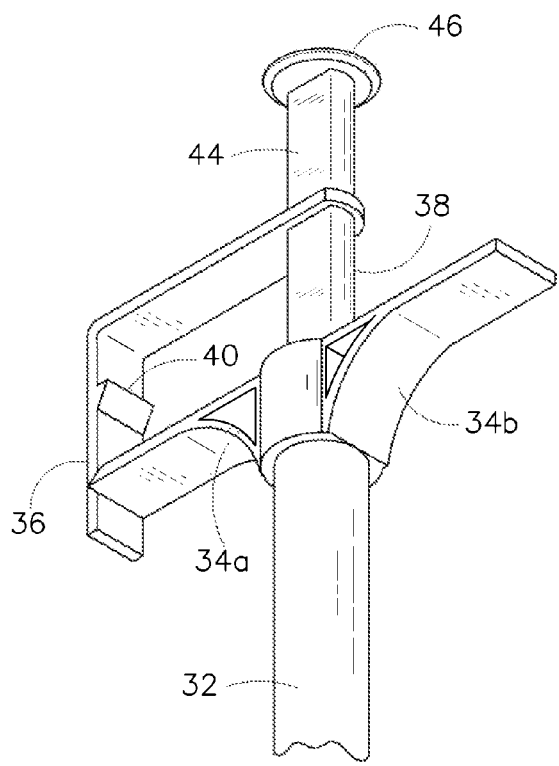
FIG. 6 is a partial perspective view of one end of the mesh placement component of FIGS. 4 and 5 according to the present invention.

Referring to FIG. 5, arm 124 of deployment sleeve 38 is pushed so that the sleeve slides within the outer housing 32, compressing spring 76, and, in turn, sliding pushrod 42. When the pushrod 42 slides relative to the outer housing 32, driving link 64a, which is pivotally attached to both pushrod 42 and needle guide 58a, forces the needle guide 58a to pivot about the pin 60a that is retained in outer housing boss 62a One other embodiment of the present invention is shown in FIGS. 8-12. It should be again understood that, in the interest of clarity, only one-half of the instrument is being shown. The other half is quite similar in function and structure as the half described herein. The upper portion of the device is similar in construction and materials to the previously disclosed embodiments, and is not repeated here.

A mesh placement device 196 includes an outer housing 198 having bosses 200 into which a pin 202 is rotatably inserted. The pin 202 is secured to an arm 204, which is attached to a needle carrier 206. A pin 208 on needle carrier 206 is rotatably inserted into a hole 210 in a link 212. Another pin 214 is secured to a pushrod 216 and is rotatably inserted into another hole 218 in the link 212. The pushrod 216 is attached to a sleeve 220 slidably disposed within the outer housing 198.

FIG. 12 shows a detail view of a needle 222 (similar to bullet needle 18) held in a recess 224 in the needle carrier 206. A thread 226, like thread 16, is attached to the needle 222 and is threaded through a slot 228 in the needle carrier 206. All components in this mechanism are preferably constructed of surgical grade stainless steel, chosen for its biocompatibility and strength.

Use and operation of this embodiment of the invention will be described beginning with reference to FIG. 8. The device 196 is introduced into the abdomen through a trocar assembly in the same manner as described in a previous embodiment. Sleeve 220 slides within the housing 198 in the direction indicated by the arrow. As shown in FIG. 9, as the sleeve 220 moves, it pushes the pushrod 216 which causes the link 212 to cause the needle carrier 206, along with the needle 222 and the thread 226, to rotate about the axis defined by the pin 202. Referring to FIG. 10, it may be seen that the needle 222 is driven into a catch 230 through an opening 232 in the outer housing 198. Accordingly, in reference to FIG. 11, it is seen that as the pushrod 216 is retracted, the link 212 is also retracted, causing the needle carrier 206 to rotate about the pivot pin 202 and back through the opening 232 into the outer housing 198, the same position as shown in FIG. 8.

Figure 13:
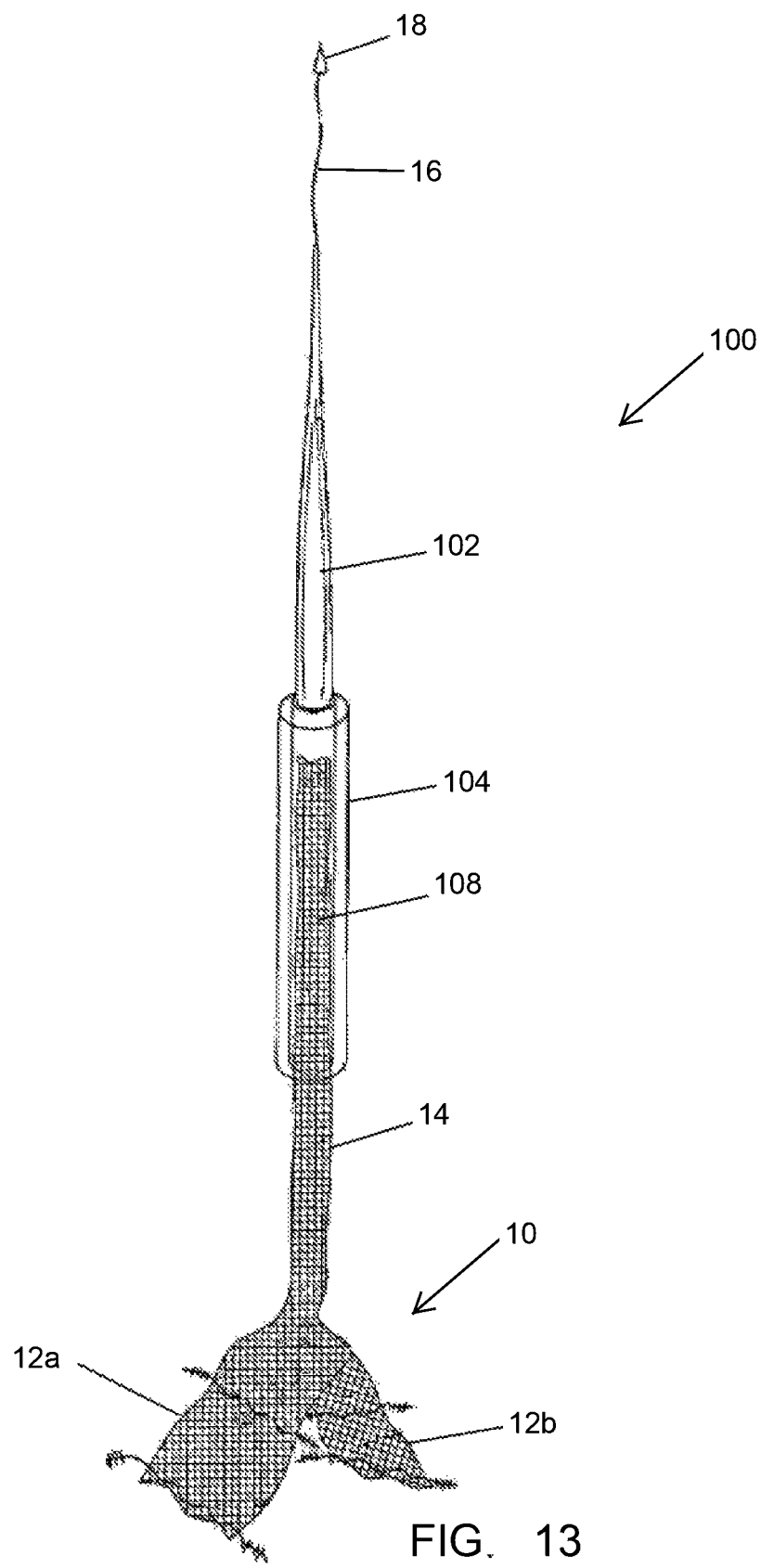
FIG. 13 is a side elevation view of the mesh graft of the present invention.
Figure 15:
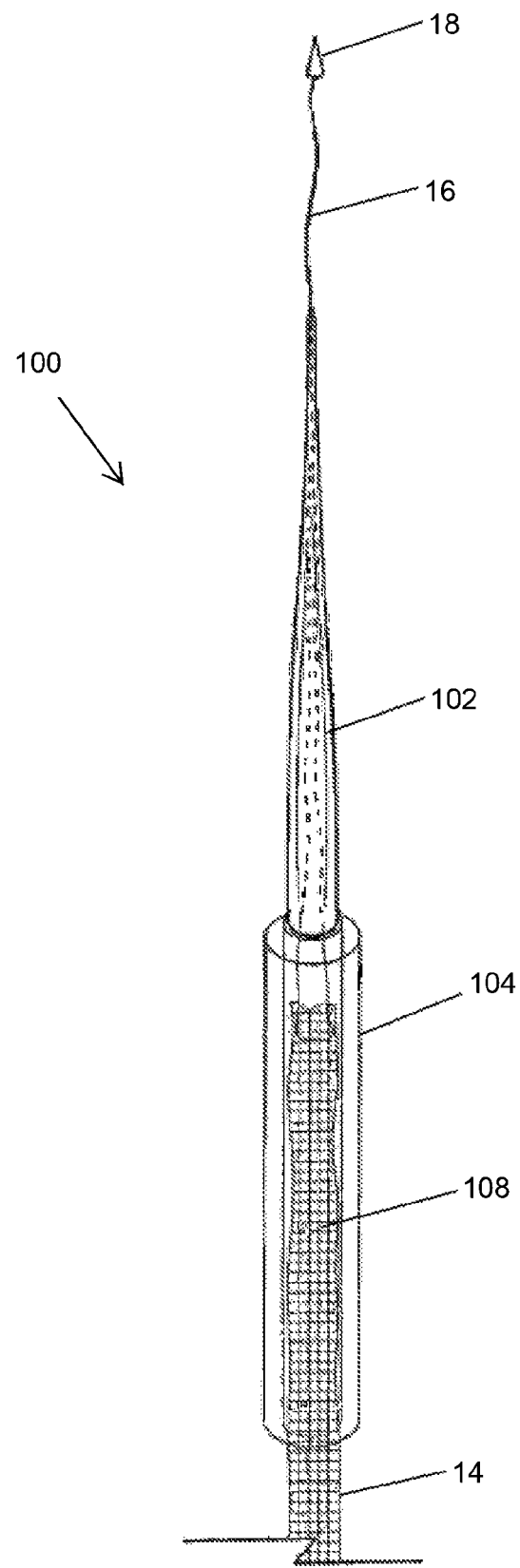
FIG. 15 is a partial side elevation view of the mesh graft of the present invention as shown in FIG. 13.

An alternative embodiment mesh delivery device may resemble the device disclosed in U.S. Pat. No. 6,936,952 and incorporated herein by reference Finally, the third component of the present invention is preferably a leg assembly 100 as illustrated in FIGS. 13 and 15. The leg assembly 100 of the present invention comprises a dilator 102 and sheath 104. The sheath 104 is configured to retain a leg 108 of the mesh 10 in place so that the leg 108 may be coupled to arcus tendineous or contralateral arcus tendineous to thereby anchor the mesh 10 for placement on one of the anterior and posterior vaginal walls. The dilator 102 is configured to open the sacrospinous ligament to thereby facilitate smooth passage of the leg 108 into position. Preferably, the dilator 102 is substantially similar to those of known prior art devices such as the Pinnacle® device. The leg assembly 100 further includes a lead suture 16 having a bullet needle 18 attached to an end thereof. The lead suture 16 will preferably be long enough to traverse to the outside of the abdomen and to a position out of the way such that the mesh 10 may be attached transabdominally, as will be described in further detail. The leg assembly 100 further comprises a mesh extension 14 member that is configured for attachment to the presacaral space. That is, the mesh extension 14 is positioned over the sacrum.

Figure 21:
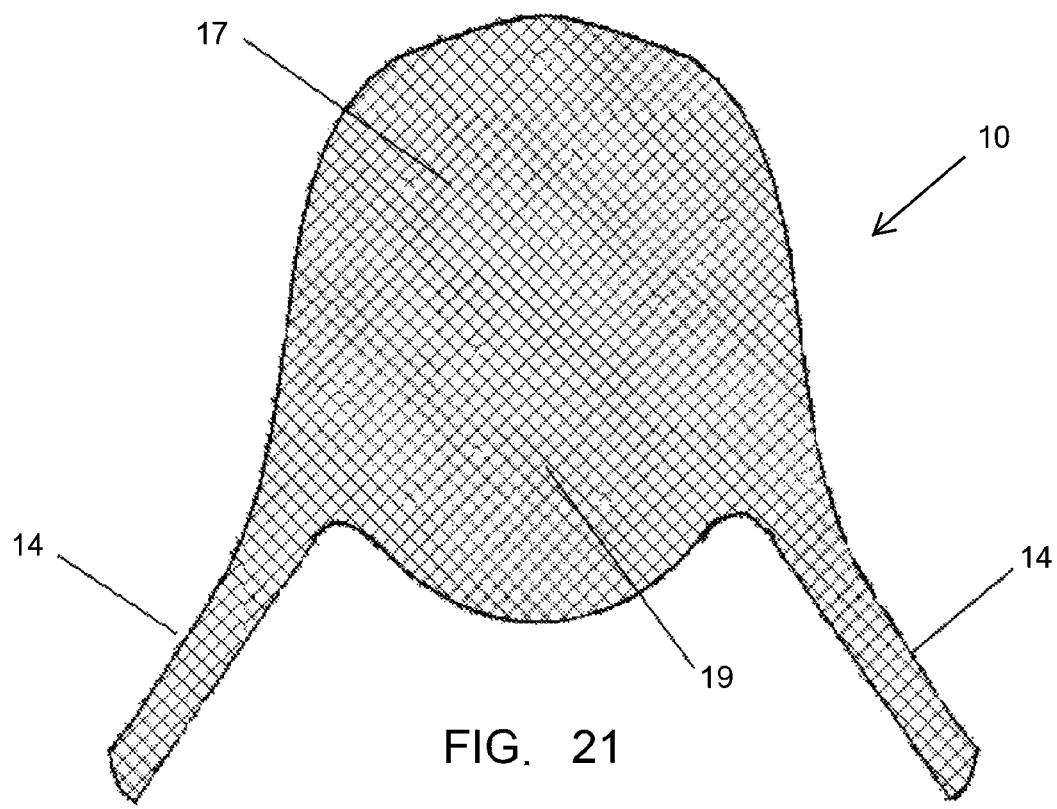
FIG. 21 is a top plan view of an illustrative embodiment of an anterior and apical mesh graft for treating vaginal prolapse according the present invention wherein the mesh extensions are configured to be fixated to the Uterosacral ligament or pelvic side wall.
Figure 22:
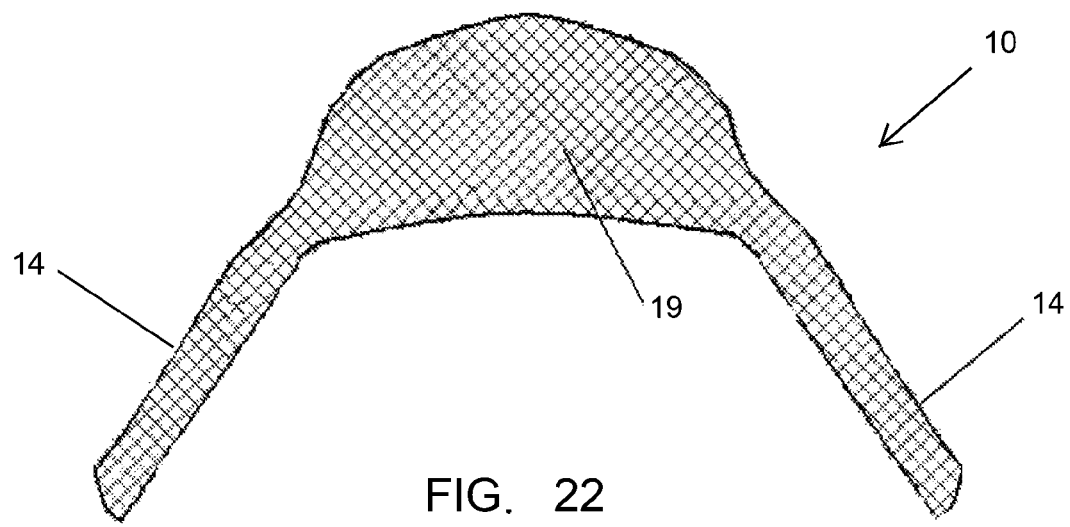
FIG. 22 is a top plan view of an illustrative embodiment of an apical mesh graft for treating vaginal prolapse according to the present invention wherein the mesh extensions are configured to be fixated to the Uterosacral ligament or pelvic side wall.
Figure 23:
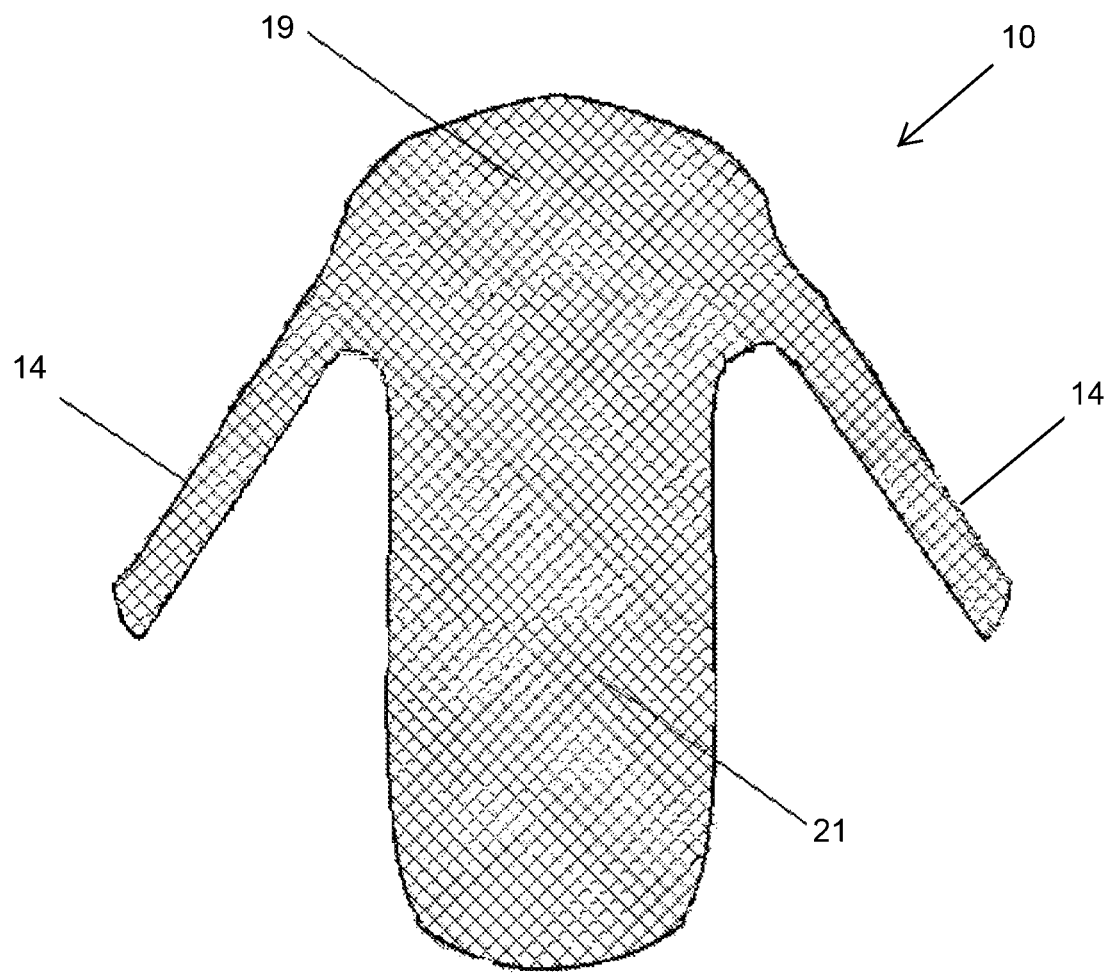
FIG. 23 is a top plan view of an illustrative embodiment of a posterior and apical mesh graft for treating vaginal prolapse according to the present invention wherein the mesh extensions are configured to be fixated to the Uterosacral ligament or pelvic side wall.
Figure 24:
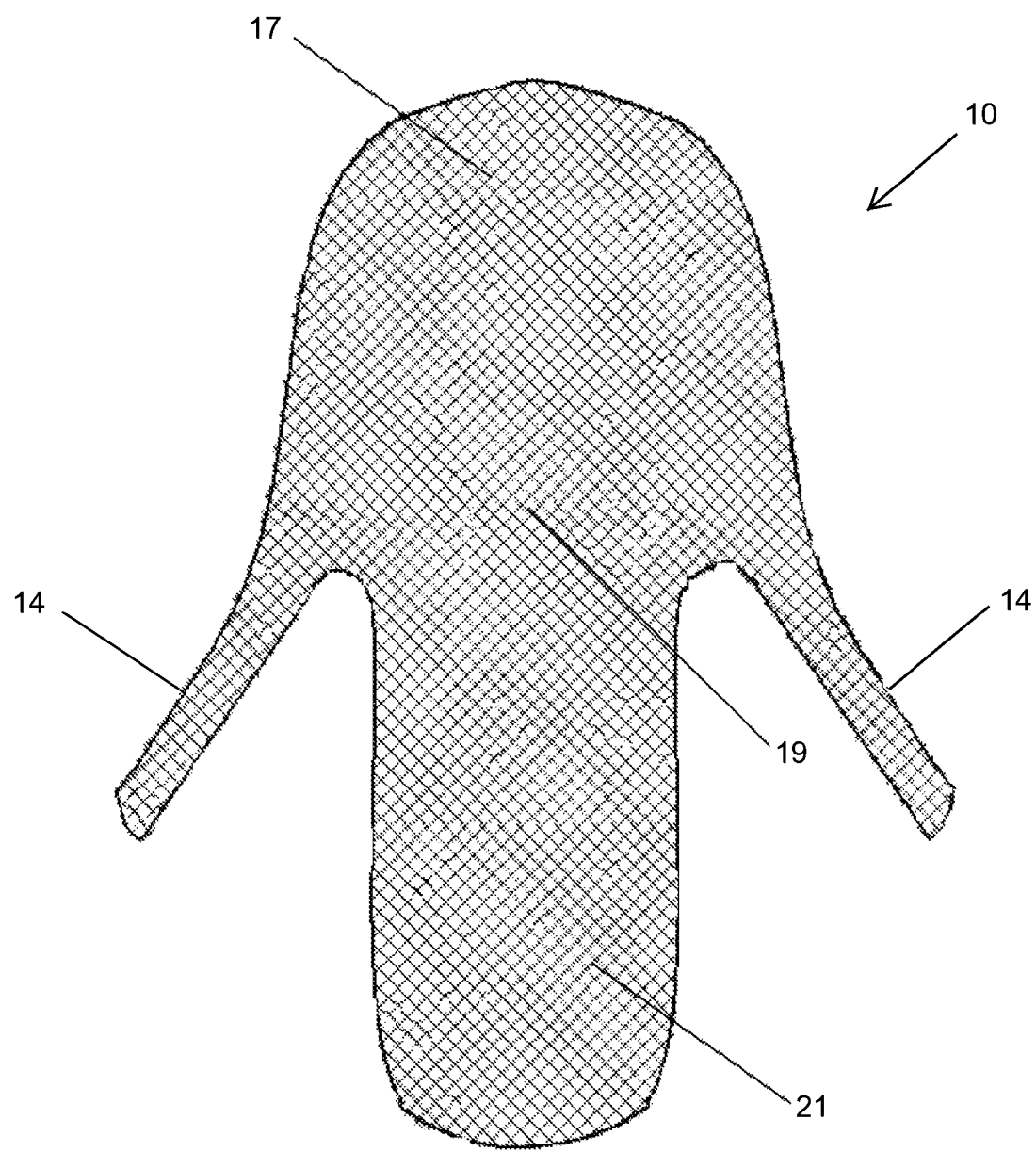
FIG. 24 is a top plan view of an illustrative embodiment of a mesh graft for treating total vaginal prolapse according to the present invention wherein the mesh extensions are configured to be fixated to the Uterosacral ligament or pelvic side wall.

In an alternative embodiment, the mesh extension 14 may be positioned and fixated in a location other than the sacrum. Such alternative fixation points may include the Uterosacral ligament or pelvic side wall from an abdominal approach. As illustrated in FIGS. 21-24, fixation of the mesh graft 10 to the Uterosacral ligament or pelvic side wall would necessitate alterations of the shape of the mesh. FIG. 21 illustrates a graft 10 suitable for anterior and apical vaginal coverage, having an anterior specific mesh coverage area 17, an apical specific mesh coverage area 19, and multiple mesh extensions 14 configured to be fixated to either the Uterosacral ligament or pelvic side wall. FIG. 22 illustrates a graft 10 suitable exclusively for apical vaginal coverage, having an apical specific mesh coverage area 19 and multiple mesh extensions 14 configured to be fixated to either the Uterosacral ligament or pelvic side wall. FIG. 23 illustrates a graft 10 suitable for posterior and apical vaginal coverage, having both an apical specific mesh coverage area 19 and a posterior specific mesh coverage area 21, as well as multiple mesh extensions 14, configured to be fixated to either the Uterosacral ligament or pelvic side wall. Lastly, FIG. 24 illustrates a graft 10 suitable for total vaginal coverage, having an anterior specific mesh coverage area 17, an apical specific mesh coverage area 19 and a posterior specific mesh coverage area 21, as well as multiple mesh extensions 14, configured to be fixated to either the Uterosacral ligament or pelvic side wall.

Of the four illustrative embodiments depicted in FIGS. 21-24, the appropriate mesh 10 shape would be chosen dependent on how much of the vagina needs coverage and which compartment is deficient. During placement of the mesh 10 embodiments illustrated in FIGS. 21-24, the anterior, apical, and posterior specific mesh coverage areas may be sewn or tacked to the corresponding vaginal wall. As described in further detail herein, the mesh extensions 14 may be sewn or tacked to the Uterosacral ligament or pelvic side wall by means of delivery device 30 in conjunction with leg assemblies 100, or by any alternative fixation means as is known in the art. It should also be noted that the lengths of mesh extension 14 may extend beyond the lengths depicted in FIGS. 21-24, as is necessary to reach the intended anatomical fixation point.

As noted previously, the inventive mesh 10 of the present invention comprises a pair of panels 12a, 12b. One of each of the pair of panels 12a, 12b will attach to and cover the anterior vaginal wall and the other will attach to and cover the posterior vaginal wall. The panels 12a, 12b may be connected to one another to form a "Y" shape wherein the narrow mesh extensions 14 form the tail portion thereof. Alternatively, panels 12a, 12b may be separate pieces that may be coupled to one another. The size of the mesh panels 12a, 12b may be variable but the panels 12a, 12b must conform to the size and shape of the vaginal wall. In one embodiment, the panels 12a, 12b would be approximately 5 cm in length and 3 cm wide and have a substantially rectangular shape. The narrow mesh extension portion may be 1-2 cm wide and 10-15 cm long.

Referring now to FIG. 14, the mesh 10, according to the present invention, is shown coupled to an anterior wall 111 and posterior wall 113 of a vagina 115. Each of panels 12a, 12b is sutured into place to thereby couple the panels 12a, 12b to the anterior and posterior walls 111 and 113, respectively. Mesh extension 14 extends rearwardly from an apex 117 of the vagina 115 and forms a part of leg assembly 110, as previously described. As such, panels 12a, 12b may be positioned to treat vaginal prolapsed, and leg assembly 100 provides an anchoring point such that the mesh 10 is firmly secured in place.

Optionally, a fourth component may be used in practicing the present invention for manipulating the vagina during securing of the mesh. The fourth component may comprise a vaginal-shaped paddle (not shown) for insertion into the vagina. The paddle may be constructed out of silicone or other such material. The paddle comprises a flat end opposite a handle configured for grasping by the surgeon. The flat end is sized and shaped for manipulation of the vagina. Accordingly, the surgeon may use the handle to manipulate the flat end of the paddle from outside of the patient's abdominal cavity rather than using his or her hands within the cavity to manipulate the vagina, as necessary. Thus, the paddle enables the surgeon to more easily manipulate the vagina while securing the mesh in place.

3. In Use

The present invention is configured for accessing and attaching one or more mesh graft to specific anatomic structures located deep within the pelvis. These structures are chosen due to their advantageous location and resistance to displacement. However, as noted previously, these structures are difficult to access, the procedure requires special training, and the procedure carries with it significant risks such that only a small number of surgeons are capable of performing the procedure. The following method of mesh placement is further illustrated in the flow chart 140 depicted in FIG. 25.

Figure 16:
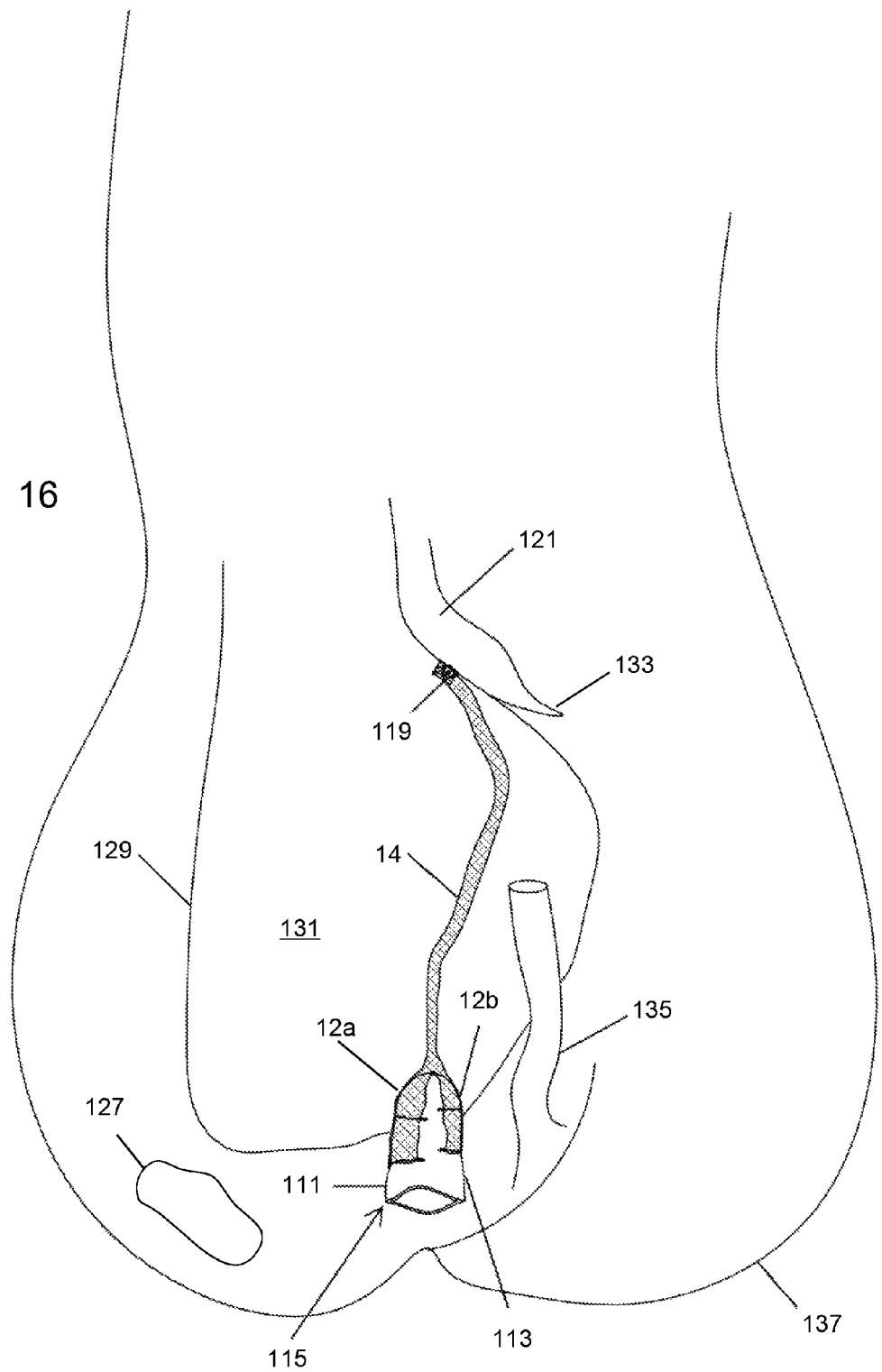
FIG. 16 is a schematic illustration showing the placement of the mesh graft of the present invention within the peritoneal cavity.
Figure 17:
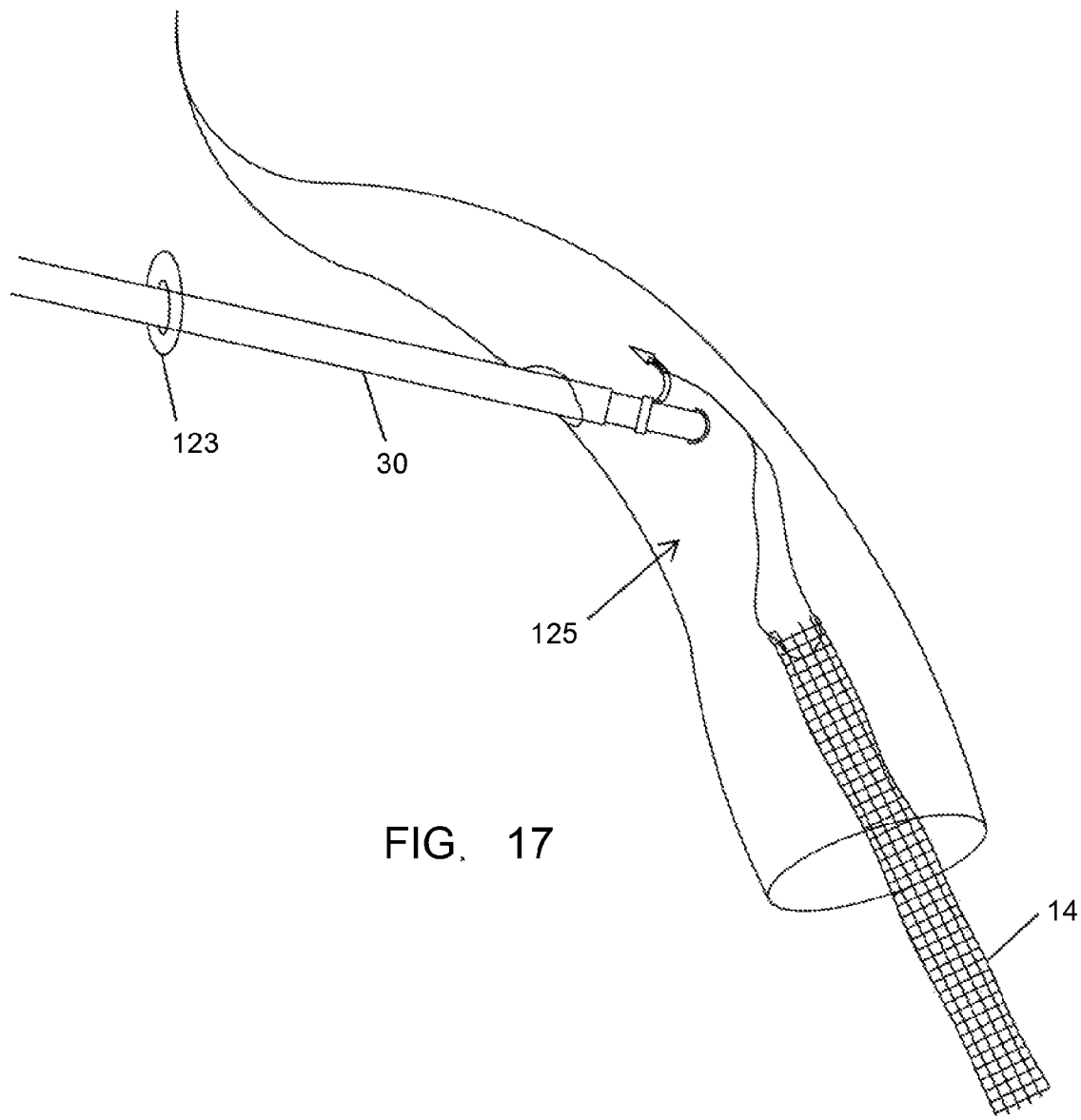
FIG. 17 is a schematic illustration of the laparoscopic placement of the mesh graft shown in FIG. 16.
Figure 18:
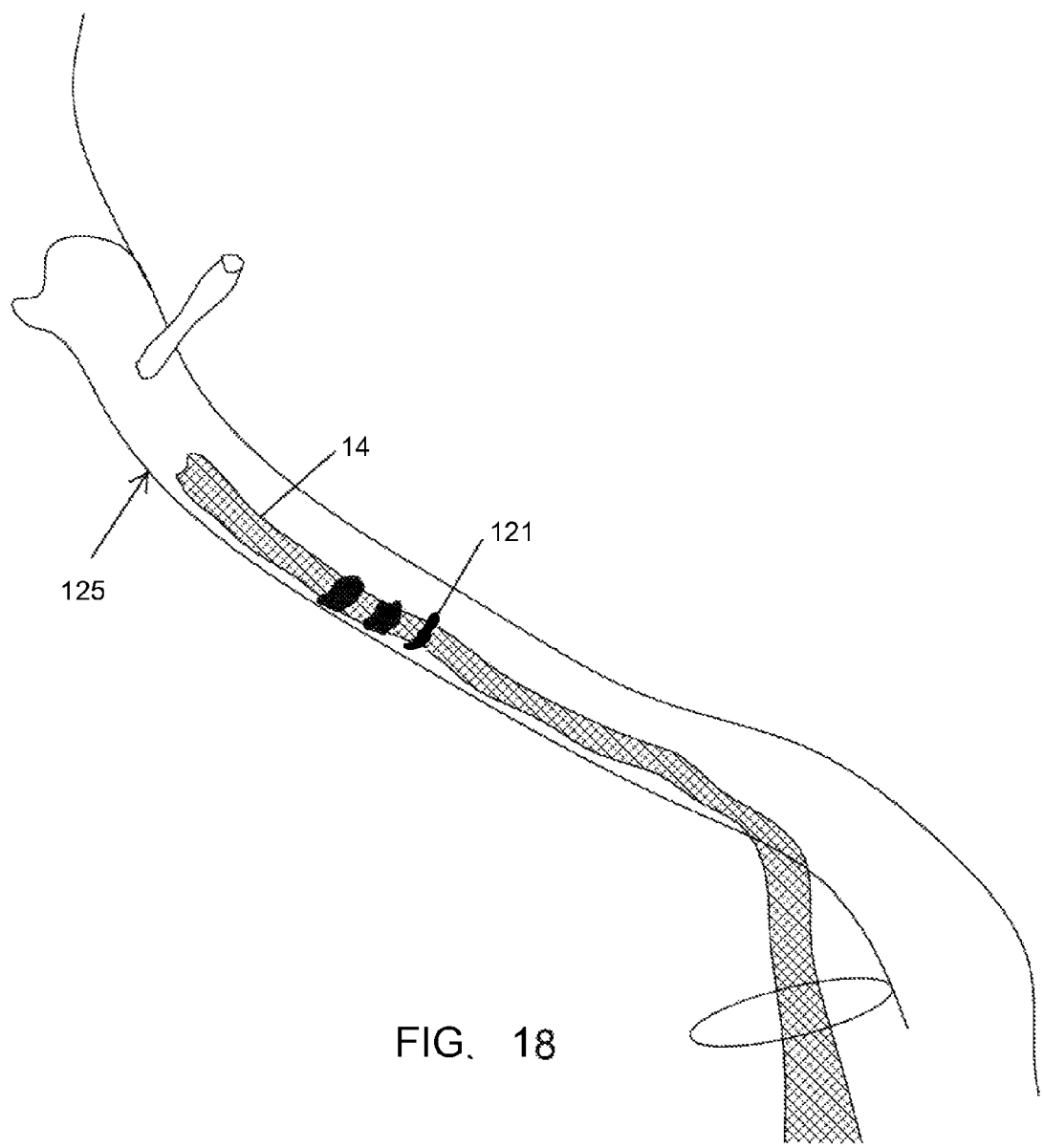
FIG. 18 is a partial schematic illustration of the laparoscopic placement of the mesh graft as shown in FIG. 17.

Referring now to FIGS. 16-18, the mesh panels 12a, 12b are introduced and laid separately upon the denuded vaginal fascia. The bodies are then secured to the anterior wall 111 and posterior wall 113 of the vagina 115, as previously described.

Once the mesh 10 and leg assembly 100 are introduced to the pelvis and subsequently affixed to the posterior 111 and anterior 113 vaginal walls, the delivery device 30 is used to put the mesh 10 in place. The delivery device 30 utilizes a needle, e.g., bullet needle 18. The needle 18 and mesh 10 are loaded into a needle guide located on the delivery device 30. Preferably, once the mesh 10 and the needle 18 are loaded into the delivery device 30, the remainder of the body of the mesh 10, i.e., the panels 12a, 12b thereof, hang from the needle 18.

After appropriate dissection of the paravaginal tissues is performed and the anchoring structures are located and cleared of any connective tissue, the delivery device 30 is positioned over the desired structure. The button 46 is then compressed thereby deploying the needle 18 such that the needle 18 and mesh 10 pass through the desired anchoring structure. Subsequently, the entire delivery device 30 is removed from the abdomen. The end of the suture protrudes from the abdomen so that it can be pulled to thereby adjust the mesh 10. i.e., the tautness or tension of the mesh as applied to the vaginal walls. Preferably, the arm or leg of the mesh loosely passes through the anchoring point. As the mesh panels 12a, 12b are already attached to the anterior and posterior wall of the vagina respectively, adjustment of the mesh extensions 14 may take place by pulling first on the suture 16 and then the dilator 102 as it is removed from the abdomen until the mesh 10 is pulled cephalad thereby causing the mesh 10 to lie flat in its respective compartment. The end of the mesh extensions 14 is then cut to release the associated needle 18 therefrom.

Referring now to FIG. 16 in particular, a schematic illustration of the attachment of the mesh 10 of the present invention is shown. As shown, the mesh 10 is attached to the anterior and posterior vaginal walls 111, 113. Mesh extension 14 extends rearwardly therefrom through the longitudinal ligaments 119 for coupling to the sacral promontory 121 where it is sutured to provide an anchoring point. By way of reference, FIG. 16 also illustrates the approximate locations of the patient's bladder 127, abdominal wall 129, peritoneal cavity 131, coccyx 133, rectum 135, and buttocks 137.

Referring now to FIGS. 17 and 18, schematic illustrations of the method of placing the mesh 10 of the present invention are shown. Referring first to FIG. 17, the delivery device 30 is shown inserted through a laparoscopic port 123 and into the peritoneum 125. As shown, the mesh extension 14 extends through the peritoneum and forwardly toward the sacral promontory. Referring now to FIG. 18, attachment of the mesh extension 14 to the sacral promontory 121 is illustrated. Accordingly, mesh extension 14 is sutured into place to provide an anchoring point to support the mesh 10 and provide a relatively secure attachment of the mesh 10 to the vaginal walls.

In addition to the above referenced method of mesh placement, FIGS. 21-24 illustrate alternative embodiments of mesh 10, in which the mesh extensions 14 may be affixed to alternative anatomical structures including the Uterosacral ligament or pelvic side wall.

It is specifically intended that the present invention not be limited to the embodiments and illustrations contained herein, but include modified forms of those embodiments including portions of the embodiments and combinations of elements of different embodiments as come within the scope of the following claims

I claim:

1. A method of treating vaginal prolapse in a patient, comprising the steps of:
   a. forming an abdominal access to the vagina;
   b. denuding a peritoneum over an anterior and posterior vaginal wall fascia;
   c. inserting at least one mesh graft and leg assembly through the abdominal access to the vagina, the leg assembly including a sheath and a dilator, the mesh graft including a first arm member, a second arm member, and a mesh extension, the mesh extension having a width smaller than widths of the first and second arm members;
   d. attaching the first arm member of the mesh graft to the anterior vaginal wall fascia;
   e. attaching the second arm member of the mesh graft to the posterior vaginal wall fascia;
   f. creating a tunnel in the peritoneum between a first incision and a second incision;
   g. passing the leg assembly through the tunnel;
   h. anchoring the mesh extension of the mesh graft to a soft tissue near a sacral promontory, the anchoring includes (1) passing a bullet needle coupled to the mesh extension through the soft tissue, (2) passing the leg assembly through the soft tissue, (3) positioning the mesh extension in the soft tissue, (4) retracting the bullet needle and leg assembly out of the abdominal access through which the at least one mesh graft and leg assembly was inserted, and (5) removing the bullet needle and leg assembly; and i. adjusting a tension of the mesh graft.

2. The method of claim 1 wherein the access is a laparoscopic portal entry.

3. The method of claim 1 wherein the access is a traditional incision.

4. The method of claim 1 wherein the mesh graft is attached to the anterior and posterior vaginal wall fascia by a suture.

5. The method of claim 4 wherein the suture is attached to the mesh graft by knot-free bidirectional fixation.

6. The method of claim 1 wherein a vaginal apex is affixed to the mesh graft at a location where the mesh extension and the first arm member connect such that the mesh extension is disposed between the vaginal apex and the soft tissue near the sacral promontory.

7. The method of claim 1 wherein the first incision is located either:
   a. near a sacral promontory,
   b. near an S1 vertebra, or
   c. near an S2 vertebra.

8. The method of claim 1 wherein the second incision is located near a posterior cul-de-sac.

9. The method of claim 1 wherein adjusting the tension of the mesh graft comprises altering a position of the mesh extension in the soft tissue including pulling a suture coupled to the mesh extension and then pulling the dilator as the dilator is removed from the abdominal access.

10. The method of claim 1, wherein the first arm member has a rectangular shape with reduced corners, and the second arm member has a tapered portion that tapers away from the mesh extension.

11. A method, comprising:
    inserting a graft into a pelvic region of a patient through an abdominal incision, the graft including a first arm member, a second arm member, and a mesh extension, the mesh extension having a width smaller than widths of the first arm member and the second arm member, a leg assembly coupled to and extending from the mesh extension of the graft, the leg assembly having a sheath, a dilator, and a bullet needle;
    coupling the mesh extension of the graft to soft tissue near a sacral promontory of the patient using a suturing device having a needle carrier and a needle catch, wherein the coupling the mesh extension of the graft to the soft tissue includes passing the bullet needle through the soft tissue by rotating the needle carrier of the suturing device and capturing the bullet needle in the needle catch of the suturing device;
    retracting the leg assembly out of the abdominal incision through which the graft was inserted;
    coupling the first arm member of the graft to an anterior vaginal wall of the patient; and
    coupling the second arm member of the graft to a posterior vaginal wall of the patient.

12. The method of claim 11, wherein the suturing device includes an outer housing, the outer housing defining a first opening and a second opening, wherein the coupling of the mesh extension of the graft to the soft tissue includes pivoting the needle carrier about an axis such that the needle carrier pivots out of the first opening and delivers the bullet needle into the needle catch via the second opening.

13. The method of claim 11, further comprising:
    inserting a paddle into the vagina of the patient; and
    applying a force to the vagina via the paddle.

14. The method of claim 11, further comprising:
    inserting a paddle into the vagina of the patient, the paddle having a flat end and a handle end;
    applying a force to the vagina via the paddle.

15. A method, comprising:
    inserting a graft into a pelvic region of a patient through an abdominal incision, the graft having a mesh extension, a first arm member, and a second arm member, the mesh extension having a width smaller than widths of the first arm member and the second arm member;
    coupling the mesh extension of the graft to soft tissue near a sacral promontory of the patient by passing a bullet needle coupled to the graft through the soft tissue by rotating a needle carrier out of an outer structure of a suturing device and capturing the bullet needle in a needle catch disposed within the outer structure of the suturing device;
    retracting the suturing device and the bullet needle from the abdominal incision through which the graft was inserted;
    coupling the first arm member of the graft to an anterior vaginal wall of the patient; and
    coupling the second arm member of the graft to a posterior vaginal wall of the patient.

16. The method of claim 15, further comprising:
    inserting a paddle into the vagina of the patient; and
    applying a force to the vagina via the paddle.

17. The method of claim 15, further comprising:
    inserting a paddle into the vagina of the patient, the paddle having a flat end and a handle end;
    applying a force to the vagina via the paddle.

* * * * *